United States Patent
Gillespie et al.

(10) Patent No.: US 12,146,113 B2
(45) Date of Patent: Nov. 19, 2024

(54) PRODUCTION OF BIO-BASED LIQUEFIED PETROLEUM GAS

(71) Applicant: LanzaTech, Inc., Skokie, IL (US)

(72) Inventors: Ralph Gillespie, Skokie, IL (US); Michelle Kocal, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 18/311,440

(22) Filed: May 3, 2023

(65) Prior Publication Data

US 2023/0340349 A1 Oct. 26, 2023

Related U.S. Application Data

(62) Division of application No. 16/774,163, filed on Jan. 28, 2020, now Pat. No. 11,680,216.

(60) Provisional application No. 62/887,125, filed on Aug. 15, 2019, provisional application No. 62/860,369, filed on Jun. 12, 2019, provisional application No. 62/798,264, filed on Jan. 29, 2019.

(51) Int. Cl.
| | |
|---|---|
| *C10L 3/12* | (2006.01) |
| *B01J 23/656* | (2006.01) |
| *B01J 31/02* | (2006.01) |
| *C07C 1/24* | (2006.01) |
| *C07C 5/03* | (2006.01) |
| *C07C 51/12* | (2006.01) |
| *C12P 7/06* | (2006.01) |
| *C12P 7/16* | (2006.01) |
| *C07C 9/08* | (2006.01) |
| *C07C 9/10* | (2006.01) |
| *C07C 53/122* | (2006.01) |

(52) U.S. Cl.
CPC ............. *C10L 3/12* (2013.01); *B01J 23/6567* (2013.01); *B01J 31/0205* (2013.01); *C07C 1/24* (2013.01); *C07C 5/03* (2013.01); *C07C 51/12* (2013.01); *C12P 7/065* (2013.01); *B01J 2531/822* (2013.01); *C07C 9/08* (2013.01); *C07C 9/10* (2013.01); *C07C 53/122* (2013.01)

(58) Field of Classification Search
None
See application file for complete search history.

(56) References Cited

U.S. PATENT DOCUMENTS

| | | | | |
|---|---|---|---|---|
| 2014/0378721 | A1* | 12/2014 | Kuwana | C07C 7/144 422/187 |
| 2017/0022124 | A1* | 1/2017 | Aribert | C07C 1/24 |
| 2017/0226538 | A1* | 8/2017 | Schultz | B01D 3/141 |

* cited by examiner

*Primary Examiner* — Youngsul Jeong (57) ABSTRACT

The disclosure provides methods for the production of liquefied petroleum gas from sustainable feedstocks, including methods comprising conversion of alcohols produced by gas fermentation for the production of propane and/or butane.

10 Claims, 6 Drawing Sheets

FIG. 1

Triglycerides

+H₂    Saturation

Hydrogenated triglycerides

+H₂    Cracking

Free fatty acids

PRODUCTION OF BIO-BASED LIQUEFIED PETROLEUM GAS

CROSS-REFERENCE TO RELATED APPLICATIONS

The application is a divisional of U.S. patent application Ser. No. 16/774,163, filed Jan. 28, 2020, which claims the benefit of U.S. Provisional Application Nos. 62/798,264, filed Jan. 29, 2019; 62/860,369, filed Jun. 12, 2019; and 62/887,125, filed Aug. 15, 2019; respectively, the contents of which are hereby incorporated by reference.

BACKGROUND

There is growing interest in using renewable resources for energy and chemical production. Carbon dioxide ($CO_2$) accounts for about 76% of global greenhouse gas emissions from human activities, with methane (16%), nitrous oxide (6%), and fluorinated gases (2%) accounting for the balance (United States Environmental Protection Agency). The majority of $CO_2$ comes from the burning of fossil fuels to produce energy, although industrial and forestry practices also emit $CO_2$ into the atmosphere. Reduction of greenhouse gas emissions, particularly $CO_2$, is critical to halt the progression of global warming and the accompanying shifts in climate and weather.

It has long been recognized that catalytic processes, such as the Fischer-Tropsch process, may be used to convert gases comprising carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases comprising $CO_2$, CO, $CH_4$, and/or $H_2$ into products such as ethanol and 2,3-butanediol.

Liquefied petroleum gas (LPG) is primarily composed of around 98% propane and/or butane with some allowable amounts of olefins such as propylene or butenes, other light hydrocarbons such as ethane, and/or heavier components. The exact composition varies by region. For example, LPG in the US is primarily propane, while in Europe it can reach up to 80% butane—there is considerable variation from country to country. The energy content of LPG ranges from about 49 to 50 MJ/kg or 25 to 28 MJ/liter.

Figure 1:
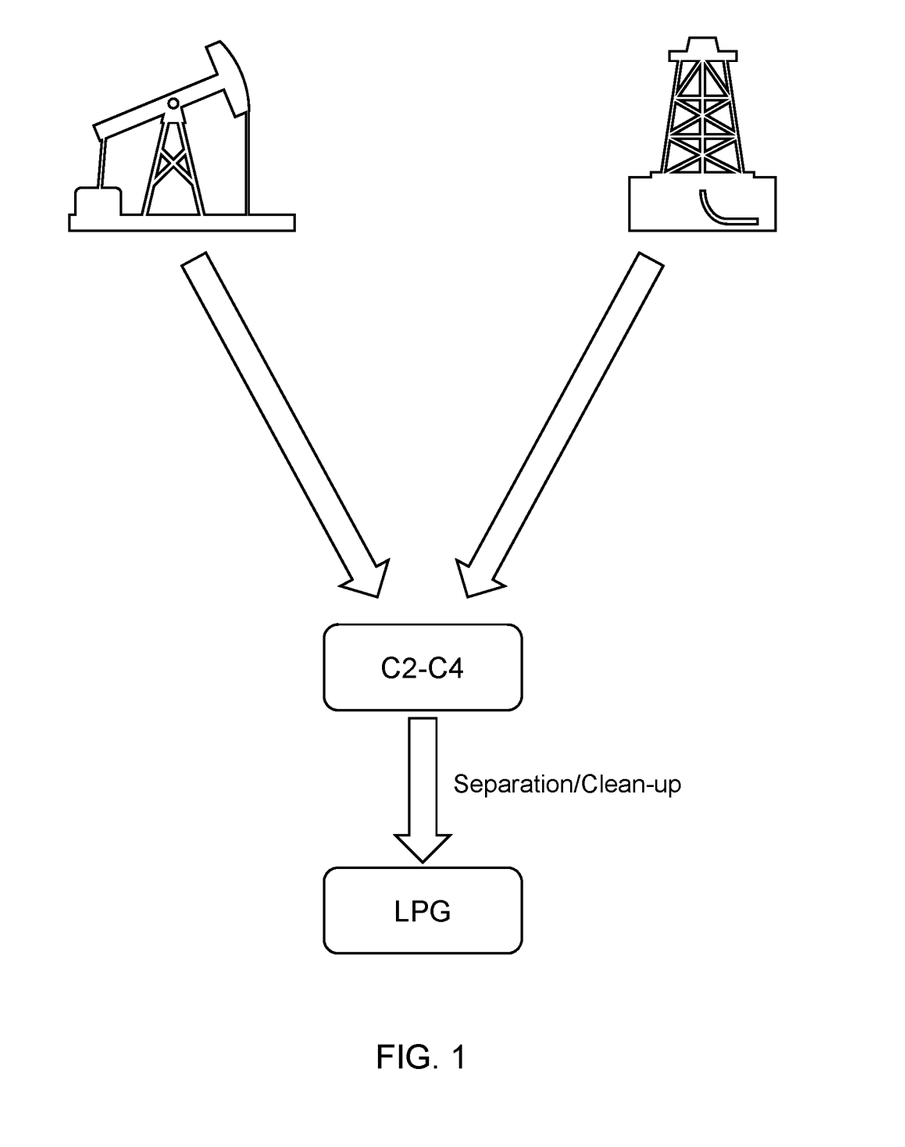
FIG. 1 shows the conventional route to LPG production, in which LPG is typically prepared by refining petroleum or "wet" natural gas, and is thus derived from fossil fuel sources, being manufactured during the refining of petroleum (crude oil), or extracted from petroleum or natural gas streams as they emerge from the ground. In some cases, C2-C4 streams refined from fossil fuel sources are highly contaminated prior to clean-up.

Typically, LPG is produced from gas wells, byproduct gas from oil wells, and off-gas from refinery processes (FIG. 1).

Figure 2:
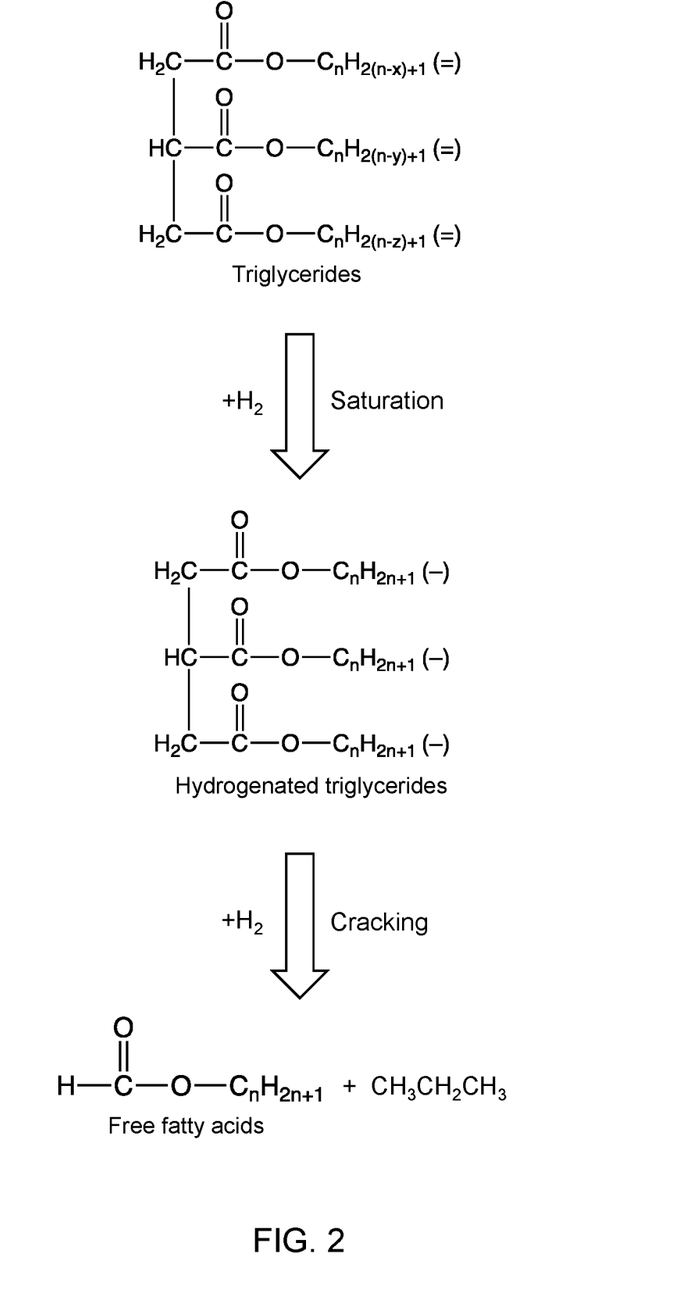
FIG. 2 shows conventional bio-based LPG production, in which propane is produced as a byproduct of triglyceride cracking (of, for example, vegetable oil/tallow sources) as fatty acids are cleaved from the glycerol backbone. Typically, propane represents only about 5% of starting carbon when produced in this manner.

In current bio-based LPG production methods (FIG. 2), the hydroprocessed esters and fatty acids (HEFA) process is used to convert tri-glycerides to primarily diesel range materials. The backbone of tri-glycerides is glycerol, which is a 3-carbon tri-alcohol. During the initial hydrogenolysis step of the HEFA process, the glycerol backbone is converted to propane as a byproduct. Although this propane qualifies as bio-based LPG because it has been produced from a waste oil, the limited amount of available waste or sustainably produced oils significantly limits the amount of LPG that can be produced in this manner (typically representing only about 5% of the starting carbon).

SUMMARY

The disclosure provides methods for producing liquefied petroleum gas from alcohols produced from bio-based or sustainable feedstocks such as waste gases, municipal solid waste (MSW), or refinery/chemical plant waste streams.

In a first aspect of the invention, the disclosure provides methods of producing liquefied petroleum gas comprising contacting a feed stream comprising a C3 alcohol, such as isopropanol and/or 1-propanol, and/or a C4 alcohol, such as butanol or an isomer of butanol, with one or more catalysts to produce a product stream comprising propane and/or butane, wherein the dehydration feed stream is a product of microbial fermentation of a gaseous substrate. In some embodiments, the one or more catalysts comprise a dehydration catalyst and/or a hydrogenation catalyst. In some embodiments, the dehydration catalyst is selected from the group consisting of acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and any combination thereof. In some embodiments, the hydrogenation catalyst comprises a Ni-alumina, Pd—C, Rancy-Ni, Co, or Pt catalyst, or any combination thereof.

In some embodiments of the first aspect, one reactor comprises the dehydration catalyst and/or the hydrogenation catalyst. In some embodiments of the first aspect, one catalyst comprises functionality of the dehydrogenation catalyst and functionality of the hydrogenation catalyst. In some embodiments of the first aspect, a dehydration reactor comprises the dehydration catalyst and a hydrogenation reactor comprises the hydrogenation catalyst.

In some embodiments of the first aspect, the method comprises (a) contacting, in the dehydration reactor, the feed stream comprising the C3 alcohol and/or the C4 alcohol with the dehydration catalyst to produce an effluent stream comprising a C3 alkene, such as propene, and/or a C4 alkene, such as butene, an isomer of butene, or butadiene; and (b) contacting, in the hydrogenation reactor, the effluent stream comprising propene and/or butene with hydrogen and the hydrogenation catalyst to produce the product stream comprising propane and/or butane.

In some embodiments, the dehydration reactor operates at a temperature of from about 100° C. to about 500° C., of from about 350° C. to about 450° C., or of from about 375° C. to about 425° C. In some embodiments, the dehydration reactor operates at a pressure of from about 0.2 MPa to about 2 MPa, of from about 0.2 MPa to about 1 MPa, or of from about 0.2 MPa to about 0.7 MPa. In some embodiments, the dehydration reactor operates at a weight hourly space velocity (whsv) of from about 1 $h^{-1}$ to about 10 $h^{-1}$, of from about 2 $h^{-1}$ to about 8 $h^{-1}$, or of from about 0.5 $h^{-1}$ to about 2 $h^{-1}$.

In some embodiments of the first aspect, the hydrogenation reactor operates at a temperature of less than about 400° C., of less than about 250° C., or of about 100° C. to about 150° C. In some embodiments, the hydrogenation reactor operates at a pressure above about 1.7 MPa (about 17 barg). In some embodiments, the hydrogenation reactor operates at a pressure above about 1.7 MPa, of about 0.7 MPa to about 8.2 MPa, of about 0.7 MPa to about 2.0 MPa, or of about 1.0 MPa to about 2.0 MPa.

In a second aspect of the invention, the disclosure provides methods of producing liquefied petroleum gas comprising: (a) contacting, in a dehydration reactor, a dehydration feed stream comprising ethanol with a catalyst to produce a first reactor effluent stream comprising ethylene; wherein the dehydration feed stream is a product of microbial fermentation of a gaseous substrate; (b) contacting, in a dimerization reactor, the first reactor effluent stream with a catalyst to produce a second reactor effluent stream comprising butene; and (c) contacting, in a hydrogenation reactor, the second reactor effluent stream and hydrogen with a catalyst to produce a product stream comprising butane.

In some embodiments, the dehydration reactor operates at a temperature of from about 100° C. to about 500° C., of from about 350° C. to about 450° C., or of from about 375° C. to about 425° C. In some embodiments, the dehydration reactor operates at a pressure of from about 0.2 MPa to about 2 MPa, of from about 0.2 MPa to about 1 MPa, or of from about 0.2 MPa to about 0.7 MPa. In some embodiments, the dehydration reactor operates at a whsv of from about 1 $h^{-1}$ to about 10 $h^{-1}$, of from about 2 $h^{-1}$ to about 8 $h^{-1}$, or of about 0.5 $h^{-1}$ to about 2 $h^{-1}$. In some embodiments, the dehydration reactor comprises a dehydration catalyst selected from the group consisting of acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and any combination thereof.

In some embodiments of the second aspect, the dimerization reactor operates at a temperature of from about 10° C. to about 150° C., of from about 24° C. to about 135° C., of from about 38° C. to about 121° C., or of about 50° C. to about 60° C. In some embodiments, the dimerization reactor operates at a pressure of about 0.7 MPa to about 6.9 MPa, of about 2.4 MPa to about 4.8 MPa, of about 2.8 MPa to about 3.4 MPa, or of about 2.0 MPa to about 2.7 MPa. In some embodiments, the dimerization reactor comprises an ionic liquid catalyst. In some embodiments, the dimerization reactor further comprises a co-catalyst or promoter. In some embodiments, the dimerization reactor comprises a Ti(IV)/AlEt$_3$ catalyst.

In some embodiments of the second aspect, the hydrogenation reactor operates at a temperature of less than about 400° C., of less than about 250° C., or of about 100° C. to about 150° C. In some embodiments, the hydrogenation reactor operates at a pressure above about 1.7 MPa (about 17 bar). In some embodiments, the hydrogenation reactor operates at a pressure above about 1.7 MPa, of about 0.7 MPa to about 8.2 MPa, of about 0.7 MPa to about 2.0 MPa, or of about 1.0 MPa to about 2.0 MPa. In some embodiments, the hydrogenation reactor comprises a Ni-alumina, Pd—C. Raney-Ni, Co, or Pt catalyst, or any combination thereof.

In a third aspect of the invention, the disclosure provides methods of producing liquefied petroleum gas comprising: (a) contacting, in a carbonylation reactor, a carbonylation feed stream comprising ethanol and carbon monoxide with a catalyst to produce a first reactor effluent stream comprising propionic acid; wherein the carbonylation feed stream is a product of microbial fermentation of a gaseous substrate; and (b) contacting, in a hydrogenation reactor, the first reactor effluent stream and hydrogen with a catalyst to produce a product stream comprising propane.

In some embodiments of the third aspect, the carbonylation feed stream comprises 1-75% water by weight. In some embodiments, the carbonylation reactor operates at a temperature of about 150° C. to about 250° C. or of about 180° C. to about 225° C. In some embodiments, the carbonylation reactor operates at a carbon monoxide partial pressure of about 0.2 MPa to about 3.0 MPa, of about 0.2 MPa to about 1.0 Mpa, or of about 0.2 MPa to about 0.3 MPa. In some embodiments, the carbonylation reactor comprises a Rh carbonyl catalyst with ethyl and iodide ligands.

In some embodiments of the third aspect, the hydrogenation reactor operates at a temperature of about 130° C. to about 200° C., of about 140° C. to about 190° C., of about 150° C. to about 180° C., or of about 150° C. to about 170° C. In some embodiments, the hydrogenation reactor operates at a pressure of about 2.0 MPa to 4.0 MPa, of about 2.5 MPa to about 3.5 MPa, or of about 2.7 to about 3.3 MPa. In some embodiments, the hydrogenation reactor comprises a Pd/Re/C catalyst.

The invention further provides a liquified petroleum gas product produced by the methods disclosed herein.

Specific embodiments of the disclosure will become evident from the following more detailed description of certain embodiments and the claims.

DETAILED DESCRIPTION

Provided herein are methods for producing liquefied petroleum gas (LPG) from alcohols that are, in some embodiments, produced from bio-based or sustainable feedstocks such as waste gases, municipal solid waste (MSW), or refinery/chemical plant waste streams. The disclosed methods provide a route to LPG production while, in some embodiments, advantageously reducing greenhouse gas (GHG) emissions.

Figure 3A:
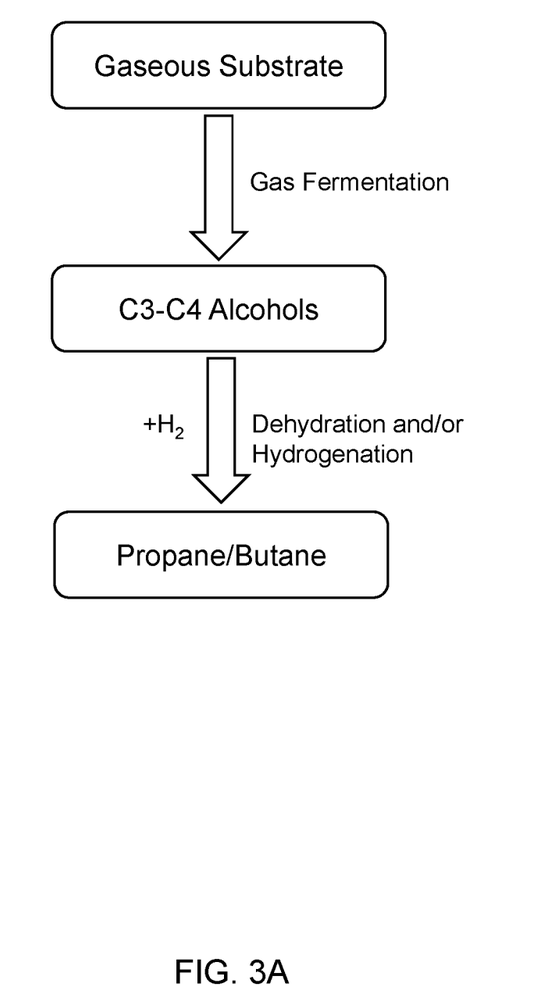
FIG. 3A shows an aspect of LPG production of the disclosure by dehydration/hydrogenation of C3-C4 alcohols in a single reactor.
Figure 3B:
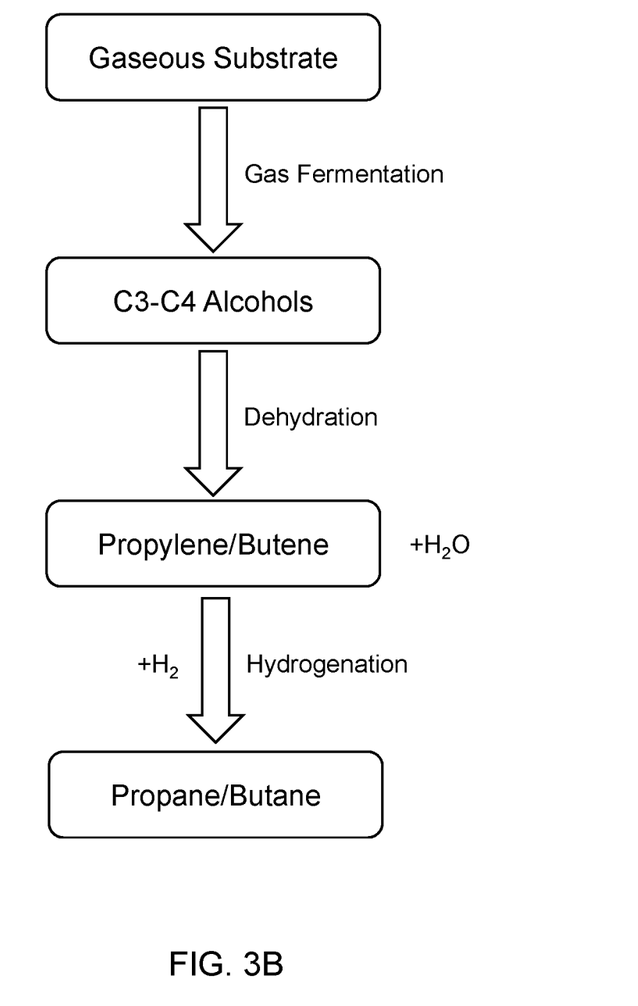
FIG. 3B shows an aspect of LPG production of the disclosure by dehydration/hydrogenation of C3-C4 alcohols in two separate reactors.

In a first route, schematically illustrated in FIG. 3A and FIG. 3B, a C3 alcohol (e.g., isopropanol) and a C4 alcohol (e.g., butanol) are produced by gas fermentation. C3-C4 alcohols can be produced either individually or in a combined manner using one or more bioreactors. The alcohols produced in this manner can be purified using fractionation, extraction, membrane separation, or any other commonly used separation technique.

In some embodiments, the method for producing liquefied petroleum gas comprises contacting, in a single reactor, a feed stream comprising a C3-C4 alcohols with a catalyst or combination of catalysts to produce a reactor effluent stream comprising propane and/or butane. The hydrogenation reactor may be operated at a temperature of about 300° C., a pressure of about 0.5 MPa, and a liquid hourly space velocity of about 1 $h^{-1}$. The hydrogenation catalyst may be a Ni or Pd catalyst. See, e.g., Grabowski et al., *Applied Catalysis A: General* 125: 129-144, 1995.

In some embodiments, C3-C4 alcohols are fed to one or more dehydration reactors using a suitable catalyst such as alumina. In some embodiments, dehydration is performed at, for example, around 400° C. and around 0.5 MPa of pressure. In some embodiments, once propene (propylene) and/or butene have been produced, they can be hydrogenated with any suitable catalyst, for example a Ni/alumina catalyst such as Ni-0750 E from BASF or Criterion KL6565, or a Pd/C catalyst such as JM 10R39. This process can be carried out in a liquid phase, vapor phase, or trickle bed reactor. In some embodiments, this process is carried out in a trickle bed and/or vapor phase reactor. In some embodiments, hydrogenation is performed at around 115° C. and around 1.0 MPa of pressure. However, the reaction can be carried out at any suitable pressure; in some embodiments, pressures above 250 psig are employed to maximize the hydrogenation rate. The reaction can be carried out at any suitable temperature with favorable equilibria for the saturation reaction, generally less than 400° C., and more favorably less than 250° C. The final step will be the separation of any remaining hydrogen and unreacted olefin from the product LPG, and recycling the hydrogen/olefin stream back to the hydrogenation reaction.

Thus, in a first aspect, the disclosure provides methods of producing liquefied petroleum gas comprising contacting a feed stream comprising a C3 alcohol and/or a C4 alcohol, such as isopropanol, 1-propanol, and/or butanol, with one or more catalysts to produce a product stream comprising propane and/or butane, wherein the dehydration feed stream is a product of microbial fermentation of a gaseous substrate. The first aspect further provides methods of producing liquefied petroleum gas comprising: (a) contacting, in a dehydration reactor, a dehydration feed stream comprising a C3 alcohol and/or C4 alcohol with a catalyst to produce a first reactor effluent stream comprising propene and/or butene; and (b) contacting, in a hydrogenation reactor, the first reactor effluent stream and hydrogen with a catalyst to produce a product stream comprising propane and/or butane.

Figure 4:
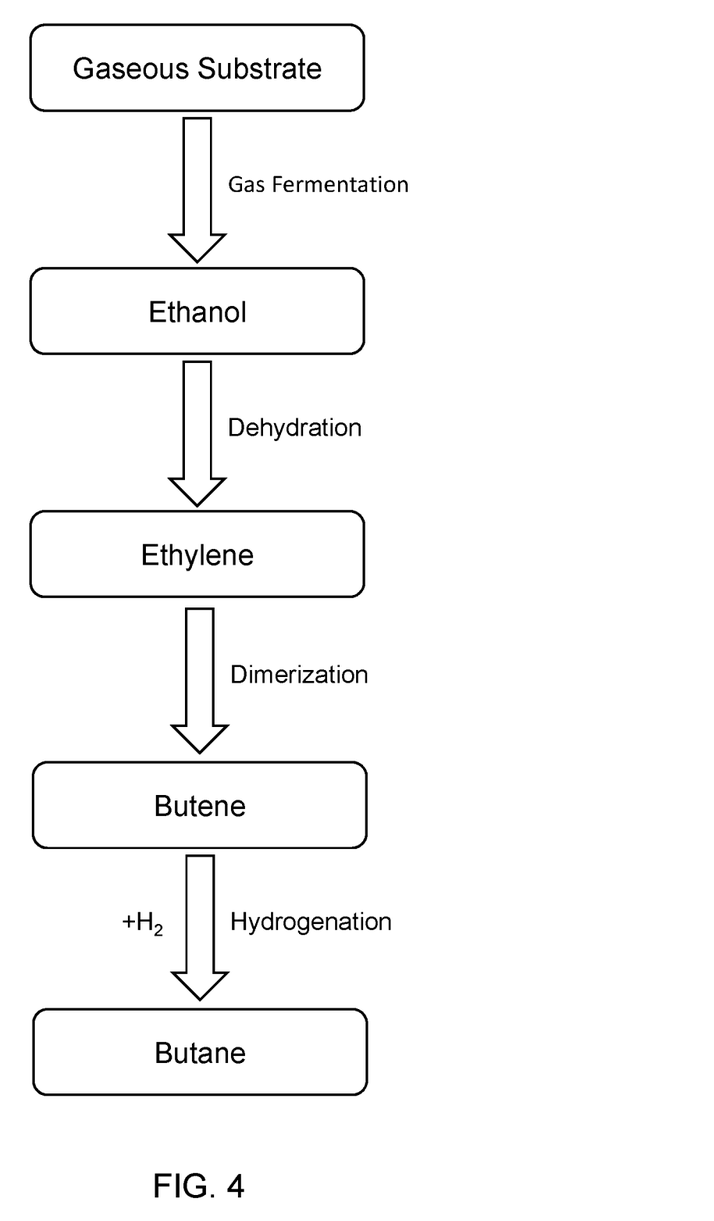
FIG. 4 shows an aspect of LPG production of the disclosure by dehydration/dimerization/hydrogenation of ethanol.

A second route, schematically illustrated in FIG. 4, can be used to convert ethanol to ethylene, dimerize to butene, and then hydrogenate to butane. Ethanol can be produced in a variety of ways, most commonly by fermentation routes. The dehydration of ethanol to ethylene is a well-known commercial process that uses commercially available catalysts such as alumina or zeolitic materials at conditions such as 400° C. at 0.5 MPa and 0.5-2 $h^{-1}$ whsv. The ethylene produced can be purified by fractionation, extraction, membrane separation, or another method to produce a product of sufficient purity to be dimerized. The dimerization can be done in a homogeneous system such as the well-known Alphabutol process or done using a heterogeneous catalyst as described in Metzger et al., *ACS Central Science* 2: 148-153, 2016. Once the 1-butene (or other butene isomer) has been produced, it can be hydrogenated as described for route 1 above, such as at 100° C. and 1.0 MPa with a Ni or Pd catalyst. Advantageously, this route can be adapted to consume sustainable ethanol feedstocks, which are readily available.

Thus, in a second aspect, the disclosure provides methods of producing liquefied petroleum gas comprising: (a) contacting, in a dehydration reactor, a dehydration feed stream comprising ethanol with a catalyst to produce a first reactor effluent stream comprising ethylene; wherein the dehydration feed stream is a product of microbial fermentation of a gaseous substrate; (b) contacting, in a dimerization reactor, the first reactor effluent stream with a catalyst to produce a second reactor effluent stream comprising butene; and (c) contacting, in a hydrogenation reactor, the second reactor effluent stream and hydrogen with a catalyst to produce a product stream comprising butane.

Figure 5:
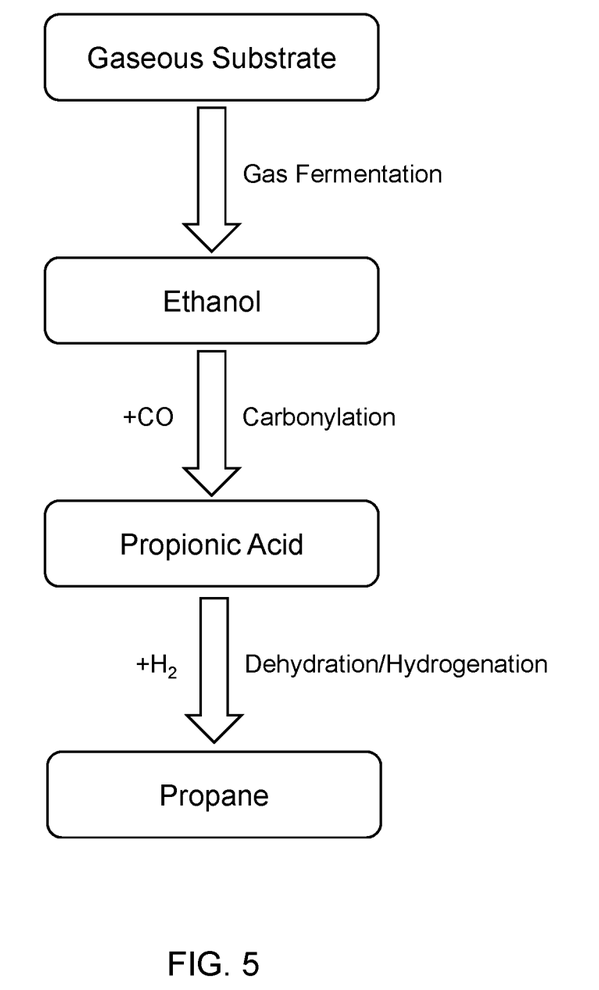
FIG. 5 shows an aspect of LPG production of the disclosure by carbonylation/hydrogenation of ethanol.

In a third route, schematically illustrated in FIG. 5, ethanol can be produced as described for the previous route. The ethanol can then be carbonylated using CO at 0.2-0.3 MPa (2-3 barg) pressure (higher pressures are also feasible) at 150-250° C. and 2500 $h^{-1}$ gas hourly space velocity (ghsv) using a Rh carbonyl catalyst with ethyl and iodide ligands. The reaction is carried out in a homogeneous reaction sparging the CO through the reactor with hydrostatic or mechanical mixing. The product is propionic acid, which can be purified by a method not limited to extraction, phase separation, and fractionation. The propionic acid thus produced can be hydrogenated to produce propane and water, which can be easily separation by condensing the water or using fractionation. Example conditions for the final step are 160° C. at 3.0 MPa hydrogen with a Pt—Re/Carbon heterogeneous catalyst. See, e.g., Ullrich and Breit, 2018, *ACS Catal.* 8: 785-89.

Thus, in a third aspect, the disclosure provides methods of producing liquefied petroleum gas comprising: (a) contacting, in a carbonylation reactor, a carbonylation feed stream comprising ethanol with carbon monoxide with a catalyst to produce a first reactor effluent stream comprising propionic acid; wherein the carbonylation feed stream is a product of microbial fermentation of a gaseous substrate; and (b) contacting, in a hydrogenation reactor, the first reactor effluent stream and hydrogen with a catalyst to produce a product stream comprising propane.

For any of the disclosed aspects, any of the feed streams and/or effluent streams may be purified or enriched in any of the desired components using any method or combination of methods known in the art, including, for example, extraction, membrane separation, fractionation, fractional distillation, evaporation, pervaporation, gas stripping, phase separation, and extractive fermentation. In some embodiments, the removed fraction is recycled back to a reactor from which an effluent stream came, especially in cases where the removed fraction comprises reagents consumed within the reactor.

Dehydration

In some embodiments of the disclosed aspects, ethanol, propanols, and butanols obtained by biochemical and/or thermochemical production routes are converted into their corresponding olefins by contacting the alcohols with a dehydration catalyst under appropriate conditions. Typical dehydration catalysts that convert alcohols such as ethanol, isopropanol, and butanol into ethylene, propylene, and butene(s) include various acid treated and untreated alumina (e.g., γ-alumina) and silica catalysts, and clays including zeolites (e.g., β-type zeolites, ZSM-5 or Y-type zeolites, fluoride-treated β-zeolite catalysts, fluoride-treated clay catalysts, etc.), sulfonic acid resins (e.g., sulfonated styrenic resins such as Amberlyst® 15), strong acids such as phosphoric acid and sulfuric acid, Lewis acids such boron trifluoride and aluminum trichloride, and many different types of metal salts including metal oxides (e.g., zirconium oxide or titanium dioxide) and metal chlorides.

Neutral alumina and zeolites can dehydrate alcohols to alkenes but generally at higher temperatures and pressures than their acidic counterparts.

In some embodiments, the dehydration catalyst comprises an acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, or a combination of any two or more of the foregoing. In some embodiments, the dehydration catalyst further comprises a modifier selected from the group consisting of Ce, Y, Sc, La, Li, Na, K, Rb, Cs, Mg, Ca, Sr, Ba, P. B, Bi, and a combination of any two or more of the foregoing. In some embodiments, the dehydration catalyst further comprises an oxide of Ti, Zr, V, Nb, Ta, Mo, Cr, W, Mn, Re, Al, Ga, In, Fc, Co, Ir, Ni, Si, Cu, Zn, Sn, Cd, P, or a combination of any two or more of the foregoing. In some embodiments, the dehydration catalyst further comprises a metal that is Cu, Ag, Au, Pt. Ni, Fc, Co, Ru, Zn, Cd, Ga, In, Rh, Pd, Ir, Re, Mn, Cr, Mo, W. Sn, Os, an alloy of any two or more of the foregoing, or a combination of any two or more of the foregoing.

In some embodiments, the dehydration catalyst comprises an aluminosilicate zeolite. In some embodiments, the dehydration catalyst further comprises a modifier that is Ga, In, Zn, Fe, Mo, Ag, Au, Ni, P, Sc, Y, Ta, a lanthanide, or a combination of any two or more of the foregoing. In some embodiments, the dehydration catalyst further comprises a metal that is Cu, Ag, Au, Pt, Ni, Fc, Co, Ru, Zn, Cd, Ga, In, Rh, Pd, Ir, Re, Mn, Cr, Mo, W, Sn. Os, an alloy of any two or more of the foregoing, or a combination of any two or more of the foregoing.

In some embodiments, the dehydration catalyst comprises a bifunctional pentasil ring-containing aluminosilicate zeolite. In some embodiments, the dehydration catalyst further comprises a modifier that is Ga, In, Zn, Fe, Mo, Ag, Au, Ni, P, Sc, Y, Ta, a lanthanide, or a combination of any two or more of the foregoing. In some embodiments, the dehydration catalyst further comprises a metal that is Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, or a combination of any two or more of the foregoing.

The dehydration reaction is conducted at a temperature and pressure where the thermodynamics are favorable. Dehydration reactions can be carried out in both gas and liquid phases with both heterogeneous and homogeneous catalyst systems in many different reactor configurations. Because water is generated in large quantities in dehydration reactions, dehydration catalysts are used that are generally tolerant to water. Typically, water is removed from the reaction zone with the product. Product alkene(s) either exit the reactor in the gas or liquid phase, depending upon reactor conditions. Water generated by the dehydration reaction may exit the reactor with unreacted alcohol and alkene product(s) and may be separated by distillation or phase separation.

In some embodiments, the feedstock of a dehydration reaction is relatively low in water content, as water can inhibit the dehydrogenation reaction. In preferred embodiments, water content in the feedstock is 50 wt % or less, 30 wt % or less, or 10 wt % or less. If a feedstock of a dehydration reaction comprises greater than 50 wt % water, such as greater than 60 wt %, greater than 70 wt %, greater than 80 wt %, or greater that 90 wt % water, a water removal step may be used prior to the dehydrogenation reaction. For example, a stripper may be used to reduce water content to about 50 wt % or lower.

In some embodiments, a fixed bed reactor is used to facilitate separation of the catalyst. In some embodiments, a two or three phase fluidized bed or the like is used. In some embodiments, the dehydration reaction is conducted using a solid catalyst, which is stable to water produced during the course of the reaction.

In some embodiments, alkene(s) produced in the dehydration reaction are isolated after the dehydration step, before being used as feedstocks for subsequent process steps (e.g., dimerization, hydrogenation, etc.). Depending on the particular configuration of the process, isolation of the alkenes after formation in the dehydration reactor can offer certain advantages, for example when the dehydration is carried out in the gas phase, while subsequent process steps are carried out in the liquid phase. However, in some embodiments, alkenes can be used directly from the product stream of the dehydration reactor without isolation (e.g., when the dehydration and the subsequent process steps are carried out under similar temperature and pressure conditions and/or when such subsequent steps are relatively insensitive to water).

Ethylene may be produced by dehydration of ethanol, and propylene may be produced by dehydration of propanol or isopropanol. However, when 1-butanol, 2-butanol, or isobutanol are dehydrated, a mixture of four C4 olefins—1-butene, cis-2-butene, trans-2-butene, and isobutene—can be formed. The exact concentration in a product stream of each butene isomer is determined by the thermodynamics of formation of each isomer. Accordingly, the reaction conditions and catalysts used can be manipulated to affect the distribution of butene isomers in the product stream. Thus, one can obtain butene mixtures enriched in a particular isomer. As a non-limiting example, isobutanol dehydration reaction conditions (e.g., reactor temperature, pressure, residence time, catalyst identity, etc.) can be adjusted to increase the relative amounts of 2-butene in a dehydration product stream.

In some embodiments of the various aspects of the invention the alcohol feedstock of the dehydration reaction comprises a mixture of alcohols including ethanol and isopropanol. This mixture, in turn, can be converted into a mixture of corresponding olefins by contacting the alcohols with a dehydration catalyst under appropriate conditions. Once the alcohol mixture has been converted into a corresponding mixture of olefins, the resulting olefins can then be separated from one another and isolated into product streams, said product streams comprising propylene, ethylene or other converted olefins.

Examples of dehydration reactions relevant to this and other aspects of the disclosure include:

$C_2H_5OH \rightarrow CH_2=CH_2+H_2O$, $C_3H_7OH \rightarrow CH_3-CH=CH_2+H_2O$, and $C_4H_9OH \rightarrow CH_3-CH=CH-CH_3+CH_3-CH_2-CH=CH_2+(etc.)+H_2O$.

In some embodiments of the various aspects of the disclosure, dehydration reactions are carried out at temperatures of from about 100 to 500° C., or of from about 350 to 450° C., or of from about 375 to 425° C., or at about 400° C. In some embodiments, dehydration reactions are carried out at a total internal reactor pressure of from about 0.2 to 2 MPa (2 to 20 barg), or of from about 0.2 to 1 MPa (2 to 10 barg), or of from about 0.2 to 0.7 MPa (2 to 7 barg), or at about 0.5 MPa (about 5 barg). In some embodiments, dehydration reactions are carried out with a whsv, defined as being the ratio of the mass flow rate of alcohols (e.g., ethanol, isopropanol, or butanol) to the mass of catalyst, of from about 1 to 10 h$^{-1}$, or of from about 2 to 8 h$^{-1}$, or of 0.5 to 2 h$^{-1}$. In some embodiments, the conversions of alcohols in the dehydration reactions are greater than 90%, or greater than 95%, or greater than 99%. See, e.g., dehydration of 1-propanol to propene as disclosed in Lepore et al., 2017, *Industrial & Engineering Chemistry Research* 56(15): 4302-4308.

Dimerization

In certain aspects of the methods disclosed herein, ethylene (produced, for example, by dehydration of ethanol) is further reacted in a dimerization reactor to produce a stream comprising butene.

Butene may be prepared from ethylene using a homogenous catalyst, for example, the Alphabutol process (see, e.g., Forestière et al., 2009, *Oil & Gas Sci. and Tech.* 6: 649-67), or by using a heterogeneous catalyst as described in Metzger et al., *ACS Central Science* 2: 148-153, 2016.

The Alphabutol process employs a liquid phase proprietary soluble catalyst system of Ti(IV)/AlEt$_3$ in the dimerization of ethylene to 1-butene at relatively high purity. Ethylene is fed to a continuous liquid phase dimerization reactor. A pump-around system removes the exothermic heat of reaction from the reactor.

The Alphabutol catalyst is the product of a reaction in the reaction medium between two components: a catalyst precursor mixture containing a titanium-based active metal and a cocatalyst diluted in 1-butene. These two components are separately and continuously injected into the reaction loop and react in situ to produce the catalyst. The principle catalytic step involves the coupling of two molecules of ethylene on the active titanium center to form a titanium (IV) heterocycle which then decomposes to 1-butene by an intra-molecular β hydrogen transfer. This chemical mechanism explains the high dimer selectivity. The absence of hydride species ensures low isomerization from 1 to 2-butenes, and less than 100 ppm of internal butenes is achieved. When conditions are optimized, selectivities for 1-butene of around 93% can be attained using the Alphabutol process.

In an exemplary Alphabutol process, ethylene dimerization takes place in the liquid phase at mild conditions (for example, 50-55° C.) and under controlled catalyst and ethylene concentrations. The exothermic heat of reaction is removed by external cooling. No specific solvent is required since the reaction takes place directly in the reactant-products mixture. The reactor effluent leaves the reaction loop for a spent catalyst separation system. The spent catalyst is removed and transformed into a non-toxic material before disposal. The hydrocarbon portion is vaporized and sent to the distillation section. In some embodiments, a first distillation column separates unconverted ethylene, which is recycled to the reaction section; and a second column recovers high purity 1-butene and a C6+ gasoline cut.

In some embodiments, the feed stream used in the processes herein comprises at least 10 weight % ethylene. In some embodiments, the feed stream comprises at least 10, 20, 30, 40, 50, 60, 70, 80 or more weight % ethylene. In some embodiments, the feed stream comprises at least 20 weight % ethylene. In some embodiments, the feed stream comprises at least 40 weight % ethylene. In some embodiments, the feed stream comprises at least 50 weight % ethylene. In some embodiments, the feed stream comprises at least 60 weight % ethylene.

In some embodiments, the dimerization reaction employs a soluble catalyst system of Ti(IV)/AlEt$_3$. In some embodiments, the dimerization reaction employs an ionic liquid catalyst comprising at least two components that form a complex. In some embodiments, the ionic liquid catalyst comprises a first component and a second component. In some embodiments, the first component of the ionic liquid catalyst comprises a Lewis Acid. In some embodiments, the Lewis acid is a metal halide compound selected from components such as Lewis Acidic compounds of Group 13 metals, including aluminum halides, alkyl aluminum halide, gallium halide, and alkyl gallium halide. In some embodiments, the Lewis Acidic compound is a Group 3, 4 or 5 metal halide. Exemplary compounds include ZrCl$_4$, HfCl$_4$, NbCl$_5$, TaCl$_5$, ScCl$_3$, YCl$_3$, and mixtures thereof.

In some embodiments, the second component of the ionic liquid catalyst is an organic salt or a mixture of salts. These salts can be characterized by the general formula Q+A−, wherein Q+ is an ammonium, phosphonium, or sulfonium cation and A− is a negatively charged ion such as Cl−, Br−, ClO$_4$−, NO$_3$−, BF$_4$−, BCl$_4$−, PF$_6$−, SbF$_6$−, AlCl$_4$−, TaF$_6$−, CuC$_2$−, FeCl$_3$−, HSO$_3$−, RSO$_3$−, SO$_3$CF$_3$−, alkyl-aryl sulfonate, and benzene sulfonate (e.g., 3-sulfurtrioxyphenyl), wherein R is an alkyl group with 1-12 carbon atoms. In some embodiments, the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In some embodiments, the ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. In some embodiments, the ionic liquid catalyst is an acidic haloaluminate ionic liquid, such as an alkyl substituted pyridinium chloroaluminate or an alkyl substituted imidazolium chloroaluminate.

In some embodiments, the liquid catalyst is used in about 5-30 volume % based on the total volume of the reactants. In some embodiments, the ionic liquid catalyst is used in about 5-25 volume % based on the total volume of the reactants. In some embodiments, the ionic liquid catalyst is used in about 5, 10, 15, 20, 25 or 30 volume % based on the total volume of the reactants.

In some embodiments, the dimerization catalyst comprises a co-catalyst or promoter, which comprises, for example, HCl or organic chloride or hydrogen halides or organic halides wherein halides include Cl, Br, and I ions. In some embodiments, the co-catalyst is anhydrous HCl. When organic chloride is used as the co-catalyst with the ionic liquid catalyst, HCl may be formed in situ in the reactor during the dimerization process. In some embodiments, co-catalysts or promoters are Bronsted acids. A Bronsted acid is any substance that can donate an H$^+$ ion to a base. Bronsted acids are H$^+$-ion or proton donors. Examples of Bronsted acids are HCl, HBr, HI, HF, sulfuric acid, and mixtures thereof. In some embodiments, the co-catalyst enhances the activity of the ionic liquid catalyst and improves the yield of the hydrocarbon product.

In some embodiments, the ratio of the co-catalyst to ethylene in the olefin feed is adjusted to shift the boiling point distribution of the hydrocarbon product fractions. In some embodiments, the dimerization conditions include a molar ratio of ethylene to the co-catalyst is between about 5 to about 75, between about 10 to about 50, or between about 10 to about 45. In some embodiments, the molar ratio of ethylene to the co-catalyst is about 10, about 13, about 15, about 20, about 22, about 25, about 30, about 35, about 38, about 40, about 41 or about 45.

Without being bound by any theory, it is believed that the Lewis acidity of the ionic liquid catalyst is enhanced by the Bronsted acidity of the HCl co-catalyst. With the catalyst combination of enhanced Lewis acidity promoted by a Bronsted acid, the ionic liquid catalyst system is able to activate ethylene molecules and the dimerization reaction can proceed. The chain length and shifts the carbon number distribution down as well as the boiling point distribution of the hydrocarbon product.

The dimerization process can be conducted in a semi-batch or continuous mode. Continuous refers to a process that operates (or is intended to operate) without interruption or cessation. For example, a continuous process would be one where the reactants (such as ethylene feed, the ionic liquid catalyst and the co-catalyst) are continually introduced into one or more reactors and the product feed comprising the olefin dimers is continually withdrawn. By semi-batch is meant a system that operates (or is intended to operate) with periodic interruption. For example, a semi-batch process to produce the olefin dimers would be one where the reactants are continually introduced into one or more reactors and the product feed is intermittently withdrawn.

The dimerization reaction can be conducted in any reactor that is suitable for the purpose of dimerization of ethylene in the feedstock in the presence of an ionic liquid catalyst to obtain a hydrocarbon product. Examples of reactors that can be used are continuously stirred tank reactors (CTSR), nozzle reactors (including nozzle loop reactors), tubular reactors (including continuous tubular reactors), fixed bed reactors (including fixed bed contactor reactors), and loop reactors (including static mixer loop reactors).

In some embodiments, the dimerization reaction conditions include temperatures from about 10° C. to about 149° C., or from about 24° C. to about 135° C., or from about 38° C. to about 121° C., or from about 50° C. to about 60° C.

In some embodiments, the dimerization reaction is conducted under a pressure of about 0.7 MPa-6.9 MPa (7-69 barg), or about 2.4 MPa-4.8 MPa (2.4-4.8 barg), or about 2.7 MPa-3.4 MPa (27-34 barg). In some embodiments, the dimerization reaction is conducted under a pressure of about 2.0 MPa-2.7 MPa (20-27 barg). In some embodiments, the dimerization reaction is conducted under a pressure of about 2.7 MPa (28 barg), 3.1 MPa (31 barg), 3.2 MPa (32 barg), or 3.4 MPa (34 barg).

Carbonylation

In some embodiments, the methods of the disclosure comprise contacting, in a carbonylation reactor, a carbonylation feed stream comprising ethanol with a catalyst to produce a reactor effluent stream comprising propionic acid. In some embodiments, the methods further comprise, before step (a), fermenting, in a bioreactor, a gaseous substrate to produce the carbonylation feed stream. In some embodiments, the methods further comprise contacting, in a hydrogenation reactor, the first reactor effluent stream with a catalyst to produce a product stream comprising propane towards the production of liquefied petroleum gas.

In an exemplary method of carbonylation, a first ethanol-containing feed stream and a second carbon monoxide-containing feed stream are directed to a liquid-phase carbonylation reactor, in which the carbonylation reaction occurs to form propionic acid.

In some embodiments, carbonylation reaction temperatures are from about 150 to 250° C. or from about 180 to 225° C. The carbon monoxide partial pressure in the reactor can vary widely but is typically from about 0.2 to about 3.0 MPa (about 2 to about 30 bar), such as from about 0.2 to about 1.0 MPa (about 2 to about 10 bar), or from about 0.2 to about 0.3 MPa (about 2 to about 3 bar). See, e.g., kinetics of ethanol carbonylation in Dake et al., 1984, *J. Molecular Catalysis* 24: 99-113.

In some embodiments, the carbonylation reactor is a mechanically stirred vessel, a vessel with educted or pump-around mixing, or bubble-column type vessel, with or without an agitator, within which the reacting liquid or slurry contents are maintained at a predetermined level, and which remains substantially constant during normal operation.

The carbonylation catalyst, in some embodiments, is a metal catalyst comprising a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]$-anion. Iodide salts optionally maintained in the carbonylation reaction mixtures of the processes described herein may be in the form of a soluble salt of an alkali metal or alkaline earth metal, quaternary ammonium, phosphonium salt, or mixtures thereof. In some embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541.

In some embodiments, the halogen-containing catalyst promoter of the carbonylation catalyst system comprises a halogen compound comprising an organic halide. Thus, alkyl, aryl, and substituted alkyl or aryl halides can be used. In some embodiments, the halogen-containing catalyst promoter is present in the form of an alkyl halide. In some embodiments, the halogen-containing catalyst promoter is present in the form of an alkyl halide in which the alkyl radical corresponds to the alkyl radical of the feed alcohol, which is being carbonylated. Thus, in the carbonylation of ethanol to propionic acid, the halide promoter may comprise ethyl halide, and such as ethyl iodide.

The components of the reaction medium are maintained within defined limits to ensure sufficient production of priopionic acid. The reaction medium contains a concentration of the metal catalyst, e.g. rhodium catalyst, in an amount from 100 to 3000 wppm, e.g., from 400 to 2000 wppm, or from 400 to 1500 wppm as rhodium. The concentration of water in the reaction medium is maintained to be less than 14 weight %, e.g., from 0.1 weight % to 14 weight %, from 0.2 weight % to 10 weight % or from 0.25 weight % to 5 weight %. Preferably, the reaction is conducted under low water conditions and the reaction medium contains less than 4 weight % water, e.g., less than 3.5 weight %, less than 3 weight %, or less than 2 weight %. In terms of ranges, the reaction medium contains 0.1 to 3.5 weight % water, e.g. from 0.1 to 3 weight % or from 0.5 to 2.8 weight %. The concentration of ethyl iodide in the reaction medium is maintained to be from 1 to 25 weight %, e.g., from 5 to 20 weight %, from 4 to 13.9 weight %. The concentration of iodide salt, e.g., lithium iodide, in the reaction medium is maintained to be from 1 to 25 weight %. e.g., from 2 to 20 weight %, from 3 to 20 weight %. The concentration of ethyl acetate in the reaction medium is maintained to be from 0.5 to 30 weight %, e.g., from 0.3 to 20 weight %, from 0.6 to 4.1 weight %. The foregoing amounts are based on the total weight of the reaction medium. The ranges disclosed in this application include the endpoints, subranges and individual values.

The concentration of propionic acid in the reaction medium is generally more than 30 weight %, e.g. more than 40 weight % or more than 50 weight %.

In some embodiments, the reaction rates are obtained even at low water concentrations by maintaining in the reaction medium an ester of the desired carboxylic acid and an alcohol, such as the alcohol used in the carbonylation, and an additional iodide ion that is over and above the iodide ion that is present as hydrogen iodide. In some embodiments, the ester is ethyl acetate. The additional iodide ion is in some embodiments an iodide salt, with lithium iodide (LiI) being used in certain embodiments. It has been found, as described in U.S. Pat. No. 5,001,259, that under low water concentrations, ethyl acetate and lithium iodide act as rate promoters only when relatively high concentrations of each of these components are present and that the promotion is higher when both of these components are present simultaneously.

The carbonylation reaction of ethanol to propionic acid product may be carried out by contacting the ethanol feed with gaseous carbon monoxide bubbled through an solvent reaction medium containing the rhodium catalyst, ethyl iodide (EtI) promoter, ethyl acetate (EtAc), and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of groups 1 and 2 of the IUPAC periodic table. In particular, alkali metal iodides are useful, with lithium iodide being particularly suitable.

In a low water carbonylation process, the additional iodide ion over and above the iodide ion present as hydrogen iodide is generally present in the catalyst solution in amounts such that the total iodide ion concentration is from 1 to 25 weight % and the ethyl acetate is generally present in amounts from 0.5 to 30 weight %, and the ethyl iodide is generally present in amounts from 1 to 25 weight %. The rhodium catalyst is generally present in amounts from 200 to 3000 wppm.

Hydrogenation

In each of the disclosed aspects, the methods described herein comprise hydrogenation of a C3-C4 olefin or propionic acid with a catalyst to produce a product stream comprising propane and/or butane (i.e., a liquefied petroleum gas product stream).

The olefin (i.e., propylene and/or butene) hydrogenation(s) may be performed using well-known and/or readily available commercial hydrogenation catalyst(s) at only slightly elevated temperatures and pressures (i.e., relatively mild reaction conditions). The reaction can be carried out at any suitable pressure, such as in the range of from about 0.7 to about 8.2 MPa (about 7 to about 82 barg), or from about 0.7 to 2.0 MPa, or from about 1.0 to 2.0 MPa. In some embodiments, the reaction is carried out above 1.7 MPa (about 17 barg) to maximize the hydrogenation rate.

The olefin hydrogenation reaction can be carried out at any suitable temperature with favorable equilibria for the saturation reaction, generally less than about 400° C. In some embodiments, the hydrogenation reaction is carried out at a temperature of less than 250° C.

For hydrogenation of C3-C4 olefins (see, e.g., U.S. Pat. No. 4,482,767), common hydrogenation catalysts include insoluble metals such as palladium (such as in the form Pd—C), platinum, nickel (such as in the form Raney-Ni or nickel-alumina), cobalt, or a mixture of these metals. Other non-limiting examples of catalysts for hydrogenation of olefins include Ni-0750 E (BASF), nickel supported on kieselguhr, Criterion KL6565, or JM 10R39.

In some embodiments, olefin hydrogenation is carried out in a liquid-phase, vapor-phase, and/or trickle bed reactor. In some embodiments, olefin hydrogenation is carried out in a trickle bed or in vapor phase. In some embodiments, the olefin-containing process stream is passed downward through a fixed bed of the hydrogenation catalyst as a vapor phase stream.

Following passage through the olefin hydrogenation zone, in some embodiments, a following step is separation of any remaining hydrogen and unreacted olefin from the product LPG and recycling the reagents back to the hydrogenation reaction.

In some embodiments, olefin hydrogenation is carried out in the presence of hydrogen equal to about 110 to about 130 mole percent of the stoichiometrically required amount of hydrogen. In some embodiments, hydrogen present in the feed gas stream is sufficient. In some embodiments, additional hydrogen is passed into the hydrogenation reactor. In other embodiments, no additional hydrogen is passed into the hydrogenation reactor in order to maximize utilization of feed gas hydrogen. In embodiments where additional hydrogen is passed into the hydrogenation reactor, the hydrogen or electricity used to produce the hydrogen is preferably acquired from renewable resources such as wind, solar, geothermal, or biomass.

In some aspects of the disclosure, propionic acid is hydrogenated to produce propane and water which can be easily separated by fractionation or by condensing the water. Hydrogenation of carboxylic acids, such as propionic acid, to alkanes, such as propane, can be performed using, for example, bimetallic catalysts, such as a catalyst of rhenium-palladium supported on graphite (a Pd/Rc/C catalyst) (see, e.g., Ullrich and Breit, 2018, *ACS Catal.* 8: 785-89).

In some embodiments, the carboxylic acid (e.g., propionic acid) hydrogenation reaction produces both the corresponding alcohol (e.g., propanol) and the corresponding alkane (e.g., propane), with the alcohol being the primary product in early stages of the reaction, but with hydrogenation of alcohol to furnish alkane proceeding in later stages of the reaction, particularly once the starting carboxylic acid material is consumed. In some embodiments, higher temperatures and/or pressures lead to increased selectivity of the alkane product versus the alcohol product. Thus, in some embodiments, hydrogenation of carboxylic acid to alkane is performed at a reaction temperature of about 130° C. to about 200° C., or about 140° C. to about 190° C., or about 150° C. to about 180° C., or about 150° C. to about 170° C. In some embodiments, the carboxylic acid hydrogenation reaction is performed at a temperature of about 130° C., or 140° C., or 150° C., or 160° C., or 170° C., or 180° C., or 190° C., or 200° C. In some embodiments, the carboxylic acid hydrogenation reaction is performed at a temperature of about 160° C. In some embodiments, the hydrogenation of carboxylic acid to alkane is performed at a reaction pressure of about 2.0 MPa to 4.0 MPa, or about 2.5 MPa to about 3.5 MPa, or about 2.7 to about 3.3 MPa, or about 2.0 MPa, or 2.2 MPa, or 2.4 MPa, or 2.5 MPa, or 2.6 MPa, or 2.7 MPa, or 2.8 MPa, or 2.9 MPa, or 3.0 MPa, or 3.1 MPa, or 3.2 MPa, or 3.3 MPa, or 3.4 MPa, or 3.5 MPa, or 3.6 MPa, or 3.8 MPa, or 4.0 MPa. In some embodiments, the carboxylic acid hydrogenation reaction is performed at a pressure of about 3.0 MPa.

The effluent stream of the hydrogenation zone is preferably passed through an indirect heat exchanger in which it is cooled sufficiently to effect a partial condensation of the hydrocarbons present in this stream. Such light gases as hydrogen, nitrogen, methane, and carbon dioxide are not condensed at this point. Essentially all of the saturated alkane (i.e., propane and/or butane) is preferably condensed. The condensed propane/butane is removed as an LPG stream having a low olefin content. Such low olefin contents are desirable in an LPG stream as evidenced by the fact that the olefin content is one of the quality indicators of LPG. The product LPG may be combined with other streams or may be sold or used as produced.

Fermentation

Alcohols, such as ethanol, C3 alcohols, and C4 alcohols, used to produce LPG are preferably produced by gas fermentation. For instance, microorganisms relevant to fermentation aspects of the disclosure may produce or may be engineered to produce ethanol (US 2009/0203100), isopropanol (US 2013/0224838), butanol (US 2010/0105115 and US 2011/0236941), and 2-butanol (US 2013/0330809.

The term "fermentation" should be interpreted as a metabolic process that produces chemical changes in a substrate. For example, a fermentation process receives one or more substrates and produces one or more products through utilization of one or more microorganisms. The term "fermentation," "gas fermentation" and the like should be interpreted as the process which receives one or more substrate, such as syngas produced by gasification and produces one or more product through the utilization of one or more C1-fixing microorganism. Preferably the fermentation process includes the use of one or more bioreactor. The fermentation process may be described as either "batch" or "continuous." "Batch fermentation" is used to describe a fermentation process where the bioreactor is filled with raw material, e.g. the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process where the fermentation process is extended for longer periods of time, and product and/or metabolite is extracted during fermentation. Preferably the fermentation process is continuous.

A "microorganism" is a microscopic organism, especially a bacterium, archea, virus, or fungus. Microorganisms relevant to fermentation aspects of the disclosure are typically bacteria. As used herein, recitation of "microorganism" should be taken to encompass "bacterium."

Microorganisms relevant to fermentation aspects of the disclosure may be classified based on functional characteristics. For example, microorganisms relevant to fermentation aspects of the disclosure may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

|  | Wood-Ljungdahl | C1-fixing | Anaerobe | Acetogen | Ethanologen | Autotroph | Carboxydotroph |
| --- | --- | --- | --- | --- | --- | --- | --- |
| Acetobacterium woodii | + | + | + | + | +/– [1] | + | – |
| Alkalibaculum bacchii | + | + | + | + | + | + | + |
| Blautia producta | + | + | + | + | – | + | + |
| Butyribacterium methylotrophicum | + | + | + | + | + | + | + |
| Clostridium aceticum | + | + | + | + | – | + | + |
| Clostridium autoethanogenum | + | + | + | + | + | + | + |
| Clostridium carboxidivorans | + | + | + | + | + | + | + |
| Clostridium coskatii | + | + | + | + | + | + | + |
| Clostridium drakei | + | + | + | + | – | + | + |
| Clostridium formicoaceticum | + | + | + | + | – | + | + |
| Clostridium ljungdahlii | + | + | + | + | + | + | + |
| Clostridium magnum | + | + | + | + | – | + | +/– [2] |
| Clostridium ragsdalei | + | + | + | + | + | + | + |
| Clostridium scatologenes | + | + | + | + | – | + | + |
| Eubacterium limosum | + | + | + | + | – | + | + |
| Moorella thermautotrophica | + | + | + | + | + | + | + |
| Moorella thermoacetica (formerly Clostridium thermoaceticum) | + | + | + | + | – [3] | + | + |
| Oxobacter pfennigii | + | + | + | + | – | + | + |
| Sporomusa ovata | + | + | + | + | – | + | +/– [4] |
| Sporomusa silvacetica | + | + | + | + | – | + | +/– [5] |
| Sporomusa sphaeroides | + | + | + | + | – | + | +/– [6] |
| Thermoanaerobacter kivui | + | + | + | + | – | + | – |

[1] Acetobacterium woodii can produce ethanol from fructose, but not from gas.
[2] It has not been investigated whether Clostridium magnum can grow on CO.
[3] One strain of Moorella thermoacetica, Moorella sp. HUC22-1, has been reported to produce ethanol from gas.
[4] It has not been investigated whether Sporomusa ovata can grow on CO.
[5] It has not been investigated whether Sporomusa silvacetica can grow on CO.
[6] It has not been investigated whether Sporomusa sphaeroides can grow on CO.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, microorganisms relevant to fermentation aspects of the disclosure contain a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for microorganisms relevant to fermentation aspects of the disclosure. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1 carbon source. Typically, microorganisms relevant to fermentation aspects of the disclosure are C1-fixing bacteria. In some embodiments, microorganisms relevant to fermentation aspects of the disclosure are derived from C1-fixing microorganisms identified in Table 1.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, microorganisms relevant to fermentation aspects of the disclosure are anaerobes. In some embodiments, microorganisms relevant to fermentation aspects of the disclosure are derived from anaerobes as identified in Table 1.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, Biochim Biophys Acta, 1784: 1873-1898, 2008). In particular, acetogens use the Wood-Ljungdahl pathway as a (1) mechanism for the reductive synthesis of acetyl-CoA from $CO_2$. (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, NY, 2006). All naturally occurring acetogens are C1-fixing, anaerobic, autotrophic, and non-methanotrophic. Typically, microorganisms relevant to fermentation aspects of the disclosure are acetogens. In some embodiments, microorganisms relevant to fermentation aspects of the disclosure are derived from acetogens as identified in Table 1.

An "ethanologen" is a microorganism that produces or is capable of producing ethanol. Typically, microorganisms relevant to fermentation aspects of the disclosure are ethanologens. In some embodiments, microorganisms relevant to fermentation aspects of the disclosure are derived from ethanologens as identified in Table 1.

An "autotroph" is a microorganism capable of growing in the absence of organic carbon. Instead, autotrophs use inorganic carbon sources, such as CO and/or $CO_2$. Typically, microorganisms relevant to fermentation aspects of the disclosure are autotrophs. In some embodiments, microorganisms relevant to fermentation aspects of the disclosure are derived from autotrophs as identified in Table 1.

A "carboxydotroph" is a microorganism capable of utilizing CO as a sole source of carbon and energy. Typically, microorganisms relevant to fermentation aspects of the disclosure are carboxydotrophs. In some embodiments, microorganisms relevant to fermentation aspects of the disclosure are derived from carboxydotrophs as identified in Table 1.

A "methanotroph" is a microorganism capable of utilizing methane as a sole source of carbon and energy. In some embodiments, microorganisms relevant to fermentation aspects of the disclosure are methanotrophs or are derived from methanotrophs. In other embodiments, microorganisms relevant to fermentation aspects of the disclosure are not methanotrophs or are not derived from methanotrophs.

More broadly, microorganisms relevant to fermentation aspects of the disclosure may be derived from any genus or species identified in Table 1. For example, the microorganism may be a member of a genus selected from the group consisting of *Acetobacterium, Alkalibaculum, Blautia, Butyribacterium, Clostridium, Eubacterium, Moorella, Oxobacter, Sporomusa*, and *Thermoanaerobacter*. In particular, the microorganism may be derived from a parental bacterium selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kivui*.

In some embodiments, microorganisms relevant to fermentation aspects of the disclosure are derived from the cluster of Clostridia comprising the species *Clostridium autoethanogenum, Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*). Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693) (WO 2012/015317). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), 0-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

Metabolic engineering of microorganisms, such as Clostridia, can tremendously expand their ability to produce many important chemical molecules. However, until recently, Clostridia were considered genetically intractable and therefore generally off limits to extensive metabolic engineering efforts. In recent years several different methods for genome engineering for Clostridia have been developed including intron-based methods (ClosTron) (Kuchne, *Strain Eng: Methods and Protocols*, 389-407, 2011), allelic exchange methods (ACE) (Heap, *Nucl Acids Res*, 40: c59, 2012; Ng, *PLOS One*, 8: c56051, 2013), Triple Cross (Liew,

*Frontiers Microbiol*, 7: 694, 2016), methods mediated through I-SceI (Zhang, Journal Microbiol Methods, 108: 49-60, 2015), MazF (Al-Hinai, *Appl Environ Microbiol*, 78: 8112-8121, 2012), or others (Argyros, *Appl Environ Microbiol*, 77: 8288-8294, 2011), Cre-Lox (Ucki, mBio, 5: e01636-01614, 2014), and CRISPR/Cas9 (Nagaraju, Biotechnol Biofuels, 9: 219, 2016). However, it remains extremely challenging to iteratively introduce more than a few genetic changes, due to slow and laborious cycling times and limitations on the transferability of these genetic techniques across species. Furthermore, C1 metabolism in Clostridia is not yet sufficiently well-understood to reliably predict modifications that will maximize C1 uptake, conversion, and carbon/energy/redox flows towards product synthesis. Accordingly, introduction of target pathways in Clostridia remains a tedious and time-consuming process.

"Gaseous substrate" and "substrate" refer to a carbon and/or energy source for microorganisms relevant to fermentation aspects of the disclosure. Typically, the substrate is gaseous and comprises a C1-carbon source, for example, $CO$, $CO_2$, and/or $CH_4$. Preferably, the substrate comprises a C1-carbon source of CO or $CO+CO_2$. The substrate may further comprise other non-carbon components, such as $H_2$, $N_2$, or electrons.

The substrate for the microbial fermentation step generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. Microorganisms relevant to fermentation aspects of the disclosure typically convert at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In some embodiments, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In some embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In some embodiments, the syngas may be obtained from the gasification of municipal solid waste or industrial solid waste.

Syngas composition can be improved to provide a desired or optimum $H_2:CO:CO_2$ ratio. The syngas composition may be improved by adjusting the feedstock being fed to the gasification process. The desired $H_2:CO:CO_2$ ratio is dependent on the desired fermentation product of the fermentation process. For ethanol, the optimum $H_2:CO:CO_2$ ratio would be: $(x):(y):(x-2y/3)$, where $x>2y$, in order to satisfy the stoichiometry for ethanol production Operating the fermentation process in the presence of hydrogen has the added benefit of reducing the amount of $CO_2$ produced by the fermentation process. For example, a gaseous substrate comprising minimal $H_2$ will typically produce ethanol and $CO_2$ by the following stoichiometry [$6\,CO+3\,H_2O \rightarrow C_2H_5OH+4\,CO_2$]. As the amount of hydrogen utilized by the C1-fixing bacterium increases, the amount of $CO_2$ produced decreases [e.g., $2\,CO+4\,H_2 \rightarrow C_2H_5OH+H_2O$].

When CO is the sole carbon and energy source for ethanol production, a portion of the carbon is lost to $CO_2$ as follows:

$$6CO+3H_2O \rightarrow C_2H_5OH+4CO_2\ (\Delta G°=-224.90\text{ KJ/mol ethanol})$$

As the amount of $H_2$ available in the substrate increases, the amount of $CO_2$ produced decreases. At a stoichiometric ratio of 2:1 ($H_2:CO$), $CO_2$ production is completely avoided.

$$5CO+1H_2+2H_2O \rightarrow 1C_2H_5OH+3CO_2\ (\Delta G°=-204.80\text{ KJ/mol ethanol})$$

$$4CO+2H_2+1H_2O \rightarrow 1C_2H_5OH+2CO_2\ (\Delta G°=-184.70\text{ KJ/mol ethanol})$$

$$CO+3H_2 \rightarrow 1C_2H_5OH+1CO_2\ (\Delta G°=-164.60\text{ KJ/mol ethanol})$$

The composition of a gaseous substrate may have a significant impact on the efficiency and/or cost of a reaction. In some embodiments, a gaseous substrate may comprise a contaminant, such as a contaminant that decreases the rate of, or prevents, a chemical reaction. The contaminant may inhibit a microorganism or the activity of a catalyst. Contaminants include, but are not limited to, sulphur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars. In particular embodiments, contaminants include hydrogen cyanide (HCN), acetylene ($C_2H_2$), BTEX (benzene, toluene, ethylbenzene, xylene), hydrogen sulfide ($H_2S$), and carbonyl sulfide (COS). The presence of oxygen may reduce the efficiency of an anaerobic fermentation process. Depending on the composition of the substrate, it may be desirable to treat, scrub, or filter the gaseous substrate to remove any undesired contaminants and/or increase the concentration of desirable components.

Typically, the fermentation is performed in a bioreactor. The term "bioreactor" includes a fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second fermentation reactor. The substrate may be provided to one or both of these reactors.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The fermentation should desirably be carried out under appropriate conditions for production of the target product. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In some embodiments, target products are recovered from the fermentation broth by continuously removing a portion of the broth from the bioreactor, separating microbial cells from the broth (conveniently by filtration), and recovering one or more target products from the broth. Alcohols may be recovered, for example, by distillation.

While the disclosure has been described in terms of various embodiments, it is understood that variations and modifications will occur to those skilled in the art. Therefore, it is intended that the appended claims cover all such equivalent variations that come within the scope of the disclosure as claimed. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

Embodiments

A first embodiment is a method of producing liquefied petroleum gas comprising contacting a feed stream comprising a C3 alcohol and/or a C4 alcohol with one or more catalysts to produce a product stream comprising propane and/or butane wherein the feed stream is a product of microbial fermentation of a gaseous substrate. Another embodiment is the first embodiment wherein the C3 alcohol comprises isopropanol and/or 1-propanol; and the C4 alcohol comprises butanol or an isomer of butanol. Another embodiment is the first Embodiment wherein the one or more catalysts comprise a dehydration catalyst and/or a hydrogenation catalyst. Another embodiment is any of the above embodiments wherein the dehydration catalyst is selected from acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and any combination thereof. Another embodiment is wherein the hydrogenation catalyst comprises a Ni-alumina, Pd—C, Rancy-Ni, Co, or Pt catalyst, or any combination thereof. Another embodiment is wherein a dehydration reactor comprises the dehydration catalyst and a hydrogenation reactor comprises the hydrogenation catalyst. Another embodiment is wherein the catalyst comprises functionality of a dehydration catalyst and functionality of a hydrogenation catalyst. Another embodiment is any of the previous embodiments comprising contacting, in the dehydration reactor, the feed stream comprising the C3 alcohol and/or the C4 alcohol with the dehydration catalyst to produce an effluent stream comprising the C3 alkene and/or the C4 alkene; and contacting, in the hydrogenation reactor, the effluent stream comprising the C3 alkene and/or the C4 alkene with hydrogen and the hydrogenation catalyst to produce the product stream comprising the propane and/or butane. Another embodiment is any of the previous embodiments wherein the C3 alkene comprises propene; and the C4 alkene comprises butene, an isomer of butene, and/or butadiene. Another embodiment is wherein the dehydration reactor operates at a temperature of from 100° C. to 500° C., of from 350° C. to 450° C., or of from 375° C. to about 425° C. Another embodiment is wherein the dehydration reactor operates at a pressure of from 0.2 MPa to 2 MPa, of from 0.2 MPa to 1 MPa, or of from 0.2 MPa to 0.7 MPa. Another embodiment is wherein the dehydration reactor operates at a weight hourly space velocity (whsv) of from 1 h$^{-1}$ to 10 h$^{-1}$, of from 2 h$^{-1}$ to 8 h$^{-1}$, or of from 0.5 h$^{-1}$ to 2 h$^{-1}$. Another embodiment is wherein the hydrogenation reactor operates at a temperature of less than 400° C., of less than 250° C., or of 100° C. to 150° C. Another embodiment is wherein the hydrogenation reactor operates at a pressure above 1.7 MPa, of 0.7 MPa to 8.2 MPa, of 0.7 MPa to 2.0 MPa, or of 1.0 MPa to 2.0 MPa.

A second embodiment is a method of producing liquefied petroleum gas comprising contacting, in a dehydration reactor, a dehydration feed stream comprising ethanol with a dehydration catalyst to produce a first reactor effluent stream comprising ethylene; wherein the dehydration feed stream is a product of microbial fermentation of a gaseous substrate; contacting, in a dimerization reactor, the first reactor effluent stream with a dimerization catalyst to produce a second reactor effluent stream comprising butene; and contacting, in a hydrogenation reactor, the second reactor effluent stream and hydrogen with a hydrogenation catalyst to produce a product stream comprising butane. Another embodiment is the second embodiment wherein the dehydration reactor operates at a temperature of from 100° C. to 500° C., of from 350° C. to 450° C., or of from 375° C. to 425° C. Another embodiment is the second embodiment wherein the dehydration reactor operates at a pressure of from 0.2 MPa to 2 MPa, of from 0.2 MPa to 1 MPa, or of from 0.2 MPa to 0.7 MPa. Another embodiment is the second embodiment wherein the dehydration reactor operates at a whsv of from 1 h$^{-1}$ to 10 h$^{-1}$, of from 2 h$^{-1}$ to 8 h$^{-1}$, or of 0.5 h$^{-1}$ to 2 h$^{-1}$. Another embodiment is the second embodiment wherein the dehydration catalyst is selected from acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and any combination thereof. Another embodiment is the second embodiment wherein the dimerization reactor operates at a temperature of from 10° C. to 150° C., of from 24° C. to 135° C., of from 38° C. to 121° C., or of from 50° C. to 60° C. Another embodiment is the second embodiment wherein the dimerization reactor operates at a pressure of 0.7 MPa to 6.9 MPa, of 2.4 MPa to 4.8 MPa, of 2.8 MPa to 3.4 MPa, or of 2.0 MPa to 2.7 MPa. Another embodiment is the second embodiment wherein the dimerization catalyst comprises an ionic liquid catalyst. Another embodiment is the second embodiment wherein the dimerization catalyst comprises a co-catalyst or a promoter. Another embodiment is the second embodiment wherein the dimerization catalyst comprises a Ti(IV)/AlEt$_3$ catalyst. Another embodiment is the second embodiment wherein the hydrogenation reactor operates at a temperature of less than 400° C., of less than 250° C., or of 100° C. to 150° C. Another embodiment is the second embodiment wherein the hydrogenation reactor operates at a pressure above 1.7 MPa, of 0.7 MPa to 8.2 MPa, of 0.7 MPa to 2.0 MPa, or of 1.0 MPa to 2.0 MPa. Another embodiment is the second embodiment wherein the hydrogenation catalyst comprises a Ni-alumina, Pd—C, Raney-Ni, Co, or Pt catalyst, or any combination thereof.

A third embodiment is a method of producing liquefied petroleum gas comprising: contacting, in a carbonylation reactor, a carbonylation feed stream comprising ethanol with carbon monoxide and a carbonylation catalyst to produce a first reactor effluent stream comprising propionic acid; wherein the carbonylation feed stream is a product of microbial fermentation of a gaseous substrate; and contacting, in a hydrogenation reactor, the first reactor effluent stream and hydrogen with a catalyst to produce a product stream comprising propane. Another embodiment is the third embodiment wherein the carbonylation reactor operates at a temperature of 150° C. to 250° C. or of 180° C. to 225° C. Another embodiment is the third embodiment wherein the carbonylation reactor operates at a carbon monoxide partial pressure of 0.2 MPa to 3.0 MPa, of 0.2 MPa to 1.0 Mpa, or of 0.2 MPa to 0.3 MPa. Another embodiment is the third embodiment wherein the carbonylation catalyst comprises a Rh carbonyl catalyst with ethyl and iodide ligands. Another embodiment is the third embodiment wherein the hydrogenation reactor operates at a temperature of 130° C. to 200° C., of 140° C. to 190° C., of 150° C. to 180° C., or of 150° C. to 170° C. Another embodiment is the third embodiment wherein the hydrogenation reactor operates at a pressure of 2.0 MPa to 4.0 MPa, of 2.5 MPa to 3.5 MPa, or of 2.7 to 3.3 MPa. Another embodiment is the third embodiment wherein the hydrogenation catalyst comprises a Pd/Re/C catalyst.

A fourth embodiment is a liquefied petroleum gas product produced by the method of any one of the previous embodiments.

The invention claimed is:

1. A method of producing liquefied petroleum gas comprising:
    a) producing a dehydration feed stream comprising a C3 alcohol and/or a C4 alcohol by microbial fermentation of a gaseous substrate comprising CO, $CO_2$, $CH_4$, or any mixture thereof, wherein the dehydration feed stream has a water content of less than 30 wt %;
    b) contacting, in a dehydration reactor, the dehydration feed stream with a dehydration catalyst to produce a first reactor effluent stream comprising a C3 alkene and/or a C4 alkene; and
    c) contacting, in a hydrogenation reactor, the first reactor effluent stream comprising the C3 alkene and/or the C4 alkene with hydrogen and a hydrogenation catalyst to produce a product stream comprising propane and/or butane.

2. The method of claim 1, wherein:
    (a) the C3 alcohol comprises isopropanol and/or 1-propanol; and
    (b) the C4 alcohol comprises butanol or an isomer of butanol.

3. The method of claim 1, wherein the dehydration catalyst is selected from acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and any combination thereof.

4. The method of claim 1, wherein the hydrogenation catalyst comprises a Ni-alumina, Pd—C, Raney-Ni, Co, or Pt catalyst, or any combination thereof.

5. The method of claim 1, wherein:
    (a) the C3 alkene comprises propene; and
    (b) the C4 alkene comprises butene, an isomer of butene, and/or butadiene.

6. The method of claim 1, wherein the dehydration reactor operates at a temperature of from 100° C. to 500° C., of from 350° C. to 450° C., or of from 375° C. to about 425° C.

7. The method of claim 1, wherein the dehydration reactor operates at a pressure of from 0.2 MPa to 2 MPa, of from 0.2 MPa to 1 MPa, or of from 0.2 MPa to 0.7 MPa.

8. The method of claim 1, wherein the dehydration reactor operates at a weight hourly space velocity (whsv) of from 1 $h^{-1}$ to 10 $h^{-1}$, of from 2 $h^{-1}$ to 8 $h^{-1}$, or of from 0.5 $h^{-1}$ to 2 $h^{-1}$.

9. The method of claim 1, wherein the hydrogenation reactor operates at a temperature of less than 400° C., of less than 250° C., or of 100° C. to 150° C.

10. The method of claim 1, wherein the hydrogenation reactor operates at a pressure above 1.7 MPa, of 0.7 MPa to 8.2 MPa, of 0.7 MPa to 2.0 MPa, or of 1.0 MPa to 2.0 MPa.

\* \* \* \* \*